United States Patent
Armstrong et al.

(10) Patent No.: US 8,852,280 B2
(45) Date of Patent: Oct. 7, 2014

(54) INTERVERTEBRAL IMPLANT

(75) Inventors: William David Armstrong, Memphis, TN (US); Stephen Edward White, Germantown, TN (US); Randall Frederick Dryer, Austin, TX (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1660 days.

(21) Appl. No.: 11/862,685

(22) Filed: Sep. 27, 2007

(65) Prior Publication Data

US 2009/0088849 A1 Apr. 2, 2009

(51) Int. Cl.
*A61F 2/44* (2006.01)
*A61F 2/30* (2006.01)
*A61B 17/86* (2006.01)
*A61F 2/28* (2006.01)

(52) U.S. Cl.
CPC ....... *A61F 2/4455* (2013.01); *A61F 2220/0025* (2013.01); *A61F 2002/30166* (2013.01); *A61B 17/86* (2013.01); *A61F 2002/30329* (2013.01); *A61F 2002/30879* (2013.01); *A61F 2230/0047* (2013.01); *A61F 2/30742* (2013.01); *A61F 2230/0028* (2013.01); *A61F 2002/30169* (2013.01); *A61F 2002/30578* (2013.01); *A61F 2002/305* (2013.01); *A61F 2002/30787* (2013.01); *A61F 2002/2835* (2013.01); *A61F 2002/30904* (2013.01); *A61F 2/30744* (2013.01); *A61F 2002/30828* (2013.01); *A61F 2002/30189* (2013.01); *A61F 2002/30892* (2013.01); *A61F 2230/0036* (2013.01)
USPC ..................... 623/17.16; 623/17.11

(58) Field of Classification Search
USPC ........................... 623/17.11–17.16; 606/86 A
See application file for complete search history.

(56) References Cited

U.S. PATENT DOCUMENTS

| | | | |
|---|---|---|---|
| 4,657,550 A | 4/1987 | Daher | |
| 4,834,757 A | 5/1989 | Brantigan | |
| 4,878,915 A | 11/1989 | Brantigan | |
| 4,904,261 A | 2/1990 | Dove et al. | |
| 4,955,908 A | 9/1990 | Frey et al. | |
| 5,192,327 A | 3/1993 | Brantigan | |
| 5,290,312 A | 3/1994 | Kojimoto et al. | |
| 5,306,309 A | 4/1994 | Wagner et al. | |
| 5,405,391 A | 4/1995 | Hednerson et al. | |
| 5,425,772 A | 6/1995 | Brantigan | |

(Continued)

FOREIGN PATENT DOCUMENTS

| | | | |
|---|---|---|---|
| EP | 0179695 A1 * | 9/1985 | |
| WO | 0224121 A2 | 3/2002 | |
| WO | 0224122 A2 | 3/2002 | |
| WO | WO 0224121 A2 * | 3/2002 | |

OTHER PUBLICATIONS

International Searching Authority, International Search Report, Dec. 22, 2008.

(Continued)

*Primary Examiner* — Pedro Philogene
*Assistant Examiner* — Lynnsy Summitt

(57) ABSTRACT

Implants for positioning between vertebral members. The implant may include a superior surface to contact against a first vertebral member, and an inferior surface to contact against a second vertebral member. The implant may include a central web that extends between first and second flanges. The flanges may be shaped to form gaps that extend the height of the implant. Spaces in communication with the gaps may be formed in an interior of the implant to hold bone growth material.

18 Claims, 10 Drawing Sheets

(56) References Cited

U.S. PATENT DOCUMENTS

| | | | | |
|---|---|---|---|---|
| 5,443,514 | A | 8/1995 | Steffee | |
| 5,514,180 | A | 5/1996 | Heggeness et al. | |
| 5,571,190 | A | 11/1996 | Ulrich et al. | |
| 5,716,415 | A | 2/1998 | Steffee | |
| 5,766,252 | A | 6/1998 | Henry et al. | |
| 5,865,845 | A | 2/1999 | Thalgott | |
| 5,888,223 | A * | 3/1999 | Bray, Jr. | 623/17.16 |
| 5,888,224 | A | 3/1999 | Beckers et al. | |
| 5,888,227 | A | 3/1999 | Cottle | |
| 5,916,267 | A * | 6/1999 | Tienboon | 623/17.11 |
| 5,984,922 | A | 11/1999 | McKay | |
| 5,989,290 | A | 11/1999 | Biedermann et al. | |
| 6,015,436 | A | 1/2000 | Schonhoffer | |
| 6,066,175 | A | 5/2000 | Henderson et al. | |
| 6,086,613 | A | 7/2000 | Camino et al. | |
| 6,106,557 | A | 8/2000 | Robioneck et al. | |
| 6,159,211 | A | 12/2000 | Boriani et al. | |
| 6,176,881 | B1 | 1/2001 | Schar et al. | |
| 6,176,882 | B1 | 1/2001 | Biedermann et al. | |
| 6,193,755 | B1 | 2/2001 | Metz-Stavenhagen et al. | |
| 6,193,756 | B1 * | 2/2001 | Studer et al. | 623/17.15 |
| 6,200,348 | B1 | 3/2001 | Biedermann et al. | |
| 6,235,059 | B1 | 5/2001 | Benezech et al. | |
| 6,245,108 | B1 | 6/2001 | Biscup | |
| 6,258,089 | B1 | 7/2001 | Campbell et al. | |
| 6,277,149 | B1 | 8/2001 | Boyle et al. | |
| 6,306,170 | B2 * | 10/2001 | Ray | 623/17.11 |
| 6,342,074 | B1 | 1/2002 | Simpson | |
| 6,375,681 | B1 | 4/2002 | Truscott | |
| 6,395,030 | B1 | 5/2002 | Songer et al. | |
| 6,432,106 | B1 | 8/2002 | Fraser | |
| 6,454,806 | B1 | 9/2002 | Cohen et al. | |
| 6,458,159 | B1 | 10/2002 | Thalgott | |
| 6,482,233 | B1 | 11/2002 | Aebi et al. | |
| 6,503,279 | B1 | 1/2003 | Webb et al. | |
| 6,520,993 | B2 | 2/2003 | James et al. | |
| 6,527,805 | B2 | 3/2003 | Studer et al. | |
| 6,558,387 | B2 | 5/2003 | Errico et al. | |
| 6,579,290 | B1 | 6/2003 | Hardcastle et al. | |
| 6,626,907 | B2 | 9/2003 | Blain et al. | |
| 6,629,998 | B1 | 10/2003 | Lin | |
| 6,635,086 | B2 | 10/2003 | Lin | |
| 6,666,889 | B1 | 12/2003 | Commarmond | |
| 6,673,075 | B2 | 1/2004 | Santilli | |
| 6,676,703 | B2 | 1/2004 | Biscup | |
| 6,682,561 | B2 | 1/2004 | Songer et al. | |
| 6,712,852 | B1 | 3/2004 | Chung et al. | |
| 6,716,245 | B2 | 4/2004 | Pasquet et al. | |
| 6,719,794 | B2 | 4/2004 | Gerber et al. | |
| 6,761,739 | B2 * | 7/2004 | Shepard | 623/17.16 |
| 6,767,366 | B2 | 7/2004 | Lee et al. | |
| 6,776,798 | B2 | 8/2004 | Camino et al. | |
| 6,790,233 | B2 * | 9/2004 | Brodke et al. | 623/17.11 |
| 6,808,538 | B2 | 10/2004 | Paponneau | |
| 6,843,805 | B2 | 1/2005 | Webb et al. | |
| 6,852,126 | B2 | 2/2005 | Ahlgren | |
| 6,899,734 | B2 | 5/2005 | Castro et al. | |
| 6,929,662 | B1 | 8/2005 | Messerli et al. | |
| 6,964,687 | B1 | 11/2005 | Bernard et al. | |
| 6,974,480 | B2 | 12/2005 | Messerli et al. | |
| 6,979,353 | B2 | 12/2005 | Bresina | |
| 6,984,234 | B2 * | 1/2006 | Bray | 606/279 |
| 7,014,659 | B2 | 3/2006 | Boyer, II et al. | |
| 7,044,972 | B2 | 5/2006 | Mathys, Jr. et al. | |
| 7,077,864 | B2 | 7/2006 | Byrd, III et al. | |
| 7,112,222 | B2 | 9/2006 | Fraser | |
| 7,135,043 | B2 | 11/2006 | Nakahara et al. | |
| 7,137,997 | B2 | 11/2006 | Paul | |
| 7,141,068 | B2 | 11/2006 | Ross | |
| 7,172,627 | B2 | 2/2007 | Fiere et al. | |
| 7,192,447 | B2 | 3/2007 | Rhoda | |
| 7,223,292 | B2 | 5/2007 | Messerli et al. | |
| 7,226,480 | B2 | 6/2007 | Thalgott | |
| 7,229,477 | B2 | 6/2007 | Biscup | |
| 7,232,464 | B2 | 6/2007 | Mathieu et al. | |
| 7,238,203 | B2 | 7/2007 | Bagga | |
| 7,618,454 | B2 * | 11/2009 | Bentley et al. | 623/17.11 |
| 2002/0099443 | A1 | 7/2002 | Messerli et al. | |
| 2003/0023312 | A1 | 1/2003 | Thalgott | |
| 2003/0028249 | A1 | 2/2003 | Baccelli et al. | |
| 2003/0083746 | A1 | 5/2003 | Kuslich | |
| 2003/0083747 | A1 | 5/2003 | Winterbottom et al. | |
| 2003/0125739 | A1 | 7/2003 | Bagga et al. | |
| 2003/0199980 | A1 | 10/2003 | Siedler | |
| 2004/0102847 | A1 | 5/2004 | Sato et al. | |
| 2004/0102850 | A1 * | 5/2004 | Shepard | 623/17.16 |
| 2004/0153160 | A1 * | 8/2004 | Carrasco | 623/17.15 |
| 2004/0172133 | A1 | 9/2004 | Messerli et al. | |
| 2004/0230305 | A1 * | 11/2004 | Gorensek et al. | 623/17.11 |
| 2005/0004671 | A1 | 1/2005 | Ross et al. | |
| 2005/0049706 | A1 * | 3/2005 | Brodke et al. | 623/17.11 |
| 2005/0055099 | A1 * | 3/2005 | Ku | 623/17.16 |
| 2005/0085910 | A1 | 4/2005 | Sweeney | |
| 2005/0085913 | A1 | 4/2005 | Fraser et al. | |
| 2005/0113922 | A1 | 5/2005 | Brazenor | |
| 2005/0125029 | A1 | 6/2005 | Bernard et al. | |
| 2005/0177238 | A1 * | 8/2005 | Khandkar et al. | 623/17.11 |
| 2005/0192577 | A1 | 9/2005 | Mosca et al. | |
| 2005/0240268 | A1 | 10/2005 | Messerli et al. | |
| 2006/0030851 | A1 | 2/2006 | Bray et al. | |
| 2006/0074488 | A1 * | 4/2006 | Abdou | 623/17.11 |
| 2006/0085071 | A1 | 4/2006 | Lechmann et al. | |
| 2006/0149371 | A1 * | 7/2006 | Marik et al. | 623/17.11 |
| 2006/0161157 | A1 | 7/2006 | Mosca et al. | |
| 2007/0073400 | A1 | 3/2007 | Paul | |
| 2007/0106384 | A1 | 5/2007 | Bray et al. | |
| 2007/0129804 | A1 * | 6/2007 | Bentley et al. | 623/17.11 |
| 2007/0129805 | A1 * | 6/2007 | Braddock et al. | 623/17.11 |
| 2007/0156240 | A1 | 7/2007 | Tsuang et al. | |
| 2007/0250167 | A1 * | 10/2007 | Bray et al. | 623/17.11 |
| 2008/0051890 | A1 * | 2/2008 | Waugh et al. | 623/17.11 |
| 2008/0249569 | A1 * | 10/2008 | Waugh et al. | 606/249 |
| 2009/0306780 | A1 * | 12/2009 | Bernard et al. | 623/17.16 |

OTHER PUBLICATIONS

International Searching Authority, Written Opinion, Dec. 22, 2008.

* cited by examiner

INTERVERTEBRAL IMPLANT

BACKGROUND

The present application relates generally to vertebral implants and methods of use, and more particularly to implants that include gaps around a periphery of the implant body.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Various conditions may lead to damage of the intervertebral discs and/or the vertebral members. The damage may result from a variety of causes including a specific event such as trauma, a degenerative condition, a tumor, or infection. Damage to the intervertebral discs and vertebral members can lead to pain, neurological deficit, and/or loss of motion.

Various procedures include replacing the entirety or a section of a vertebral member, the entirety or a section of an intervertebral disc, or both. One or more replacement implants may be inserted to replace the damaged vertebral members and/or discs. The implants may further include bone growth material to facilitate fusion of the implant to one or both adjacent vertebral members.

SUMMARY

The present application is directed to implants that fit within an intervertebral space formed between first and second vertebral members. The implant may include a body with a central web and first and second outwardly-extending flanges. The first and second flanges may be spaced apart along the central web. The body may include an exterior surface formed by one or more of the central web and the flanges. The body may further include a height defined by a superior surface that contacts the first vertebral member and an inferior surface that contacts the second vertebral member. First and second spaces may be formed within an interior of the exterior surface and may extend the height of the body. A first gap may be formed in the exterior surface on a first side of the central web, and the first gap may be in communication with the first space and extend. A second gap may be formed in the exterior surface on a second side of the central web. The second gap may be in communication with the second space and extend the height of the body.

DETAILED DESCRIPTION

Figure 1:
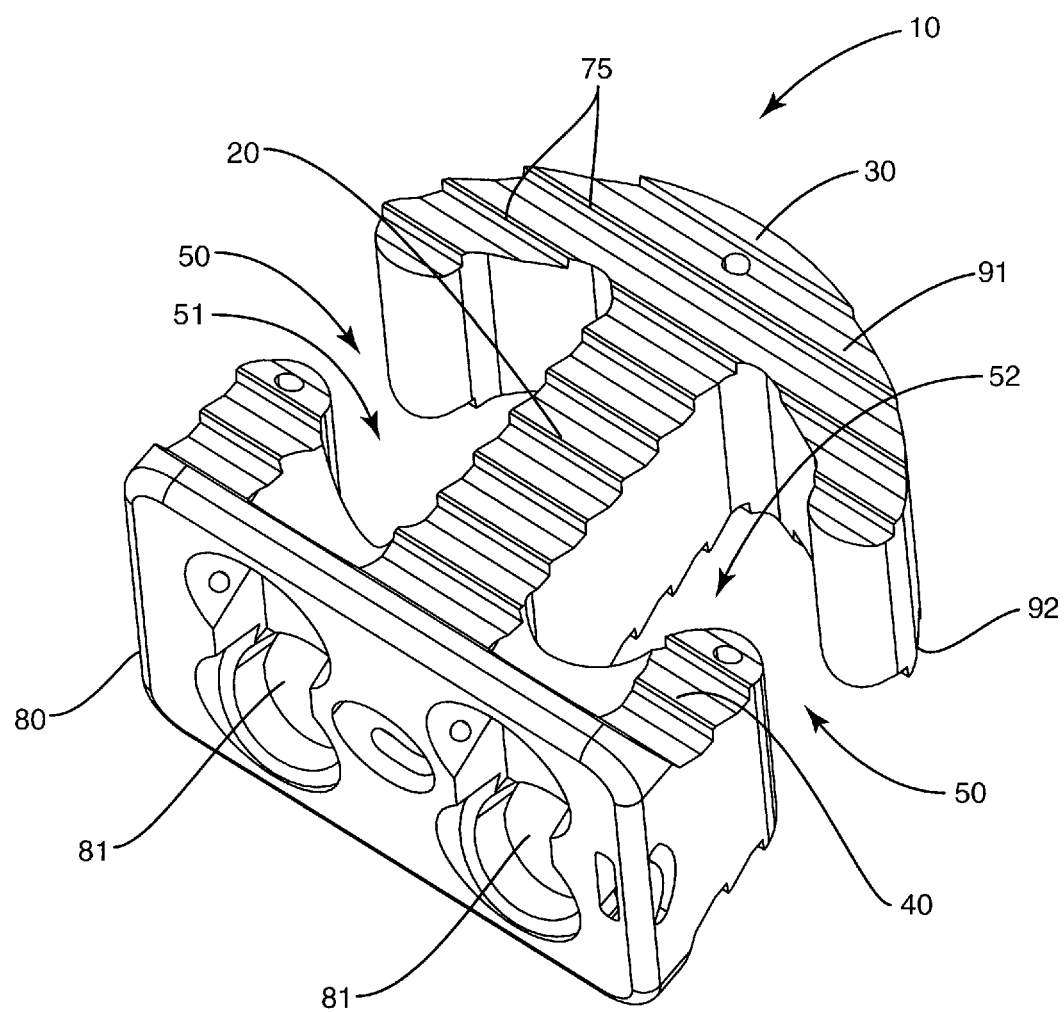
FIG. 1 is a perspective view of a implant according to one embodiment.

The present application is directed to implants for positioning within an intervertebral space formed between first and second vertebral members. FIG. 1 illustrates one embodiment of an implant 10 with a superior surface 91 to contact against a first vertebral member, and an inferior surface 92 to contact against a second vertebral member. The implant 10 includes a central web 20 that extends between first and second flanges 30, 40. The flanges 30, 40 are shaped to form gaps 50 that extend the height of the implant 10. Spaces 51, 52 in communication with the gaps 50 are formed in an interior of the implant 10 to hold bone growth material.

Figure 2:
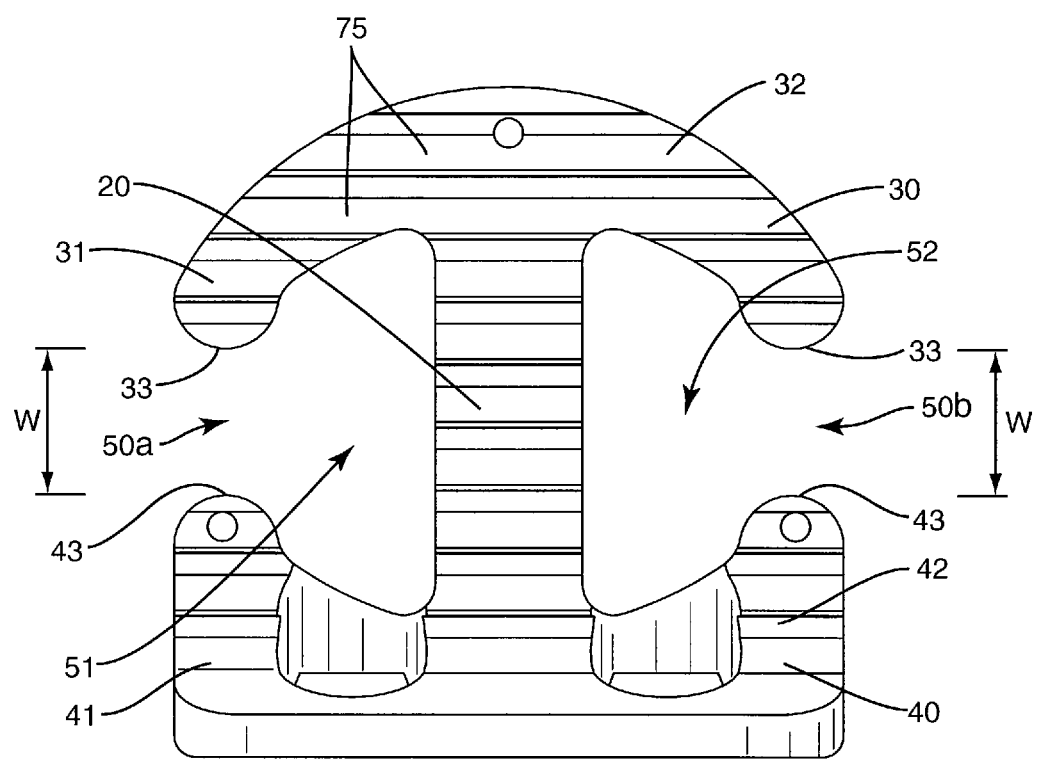
FIGS. 2-10 are top views of implants according to various embodiments.
Figure 3:
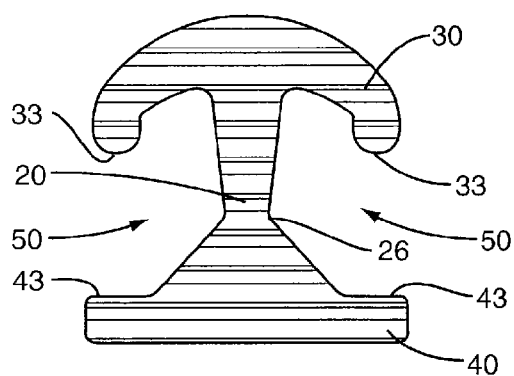

The web 20 extends between the flanges 30, 40 and forms a central section of the implant 10. Web 20 may include a variety of shapes and sizes. FIGS. 1 and 2 include the web 20 with a substantially constant width, with FIG. 3 including a web 20 with a variable width. The web 20 of FIG. 3 reduces to a neck 26 at an intermediate point between the flanges 30, 40. The width increases on each side of the neck 26 with the width being larger at the second flange 40 than at the first flange 30.

Figure 4:
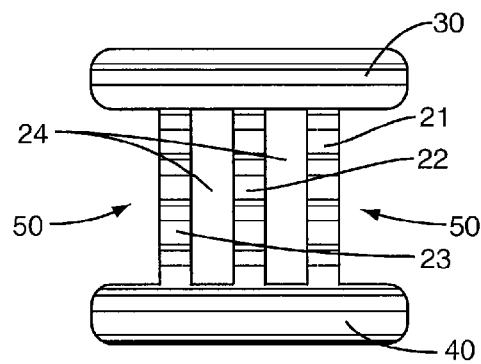
Figure 5:
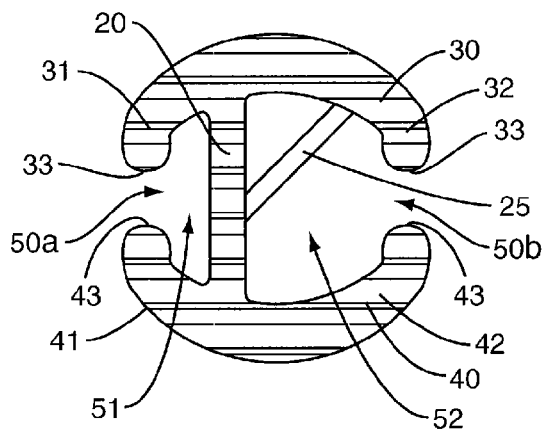

Web 20 may also include multiple different sections. FIG. 4 illustrates an embodiment with the web 20 formed by multiple sections 21, 22, 23 that are spaced apart with spaces 24 formed therebetween. The multiple sections 21, 22, 23 and spaces 24 may include the same or different shapes and sizes. FIG. 5 illustrates another embodiment including a web 20 with a brace 25 branching off and connecting with the first flange 30. In another embodiment, web 20 is constructed of a single section that includes an aperture that extends between the superior and inferior surfaces 91, 92.

Figure 6:
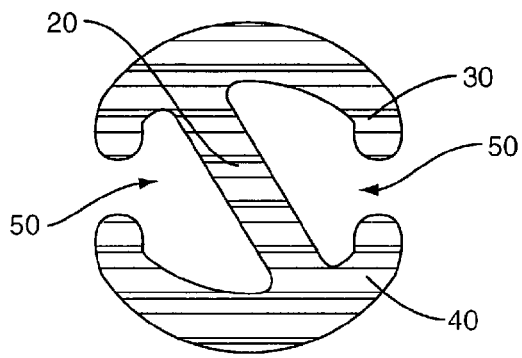

Web 20 may further be positioned at various lateral locations within the central section of the implant 10. FIGS. 1 and 2 illustrate an embodiment with the web 20 laterally centered within the implant 10 and positioned at a middle of each of the flanges 30, 40. In other embodiments as illustrated in FIG. 5, the web 20 is laterally offset away from a center of the implant 10. In some embodiments as illustrated in FIGS. 1, 2, and 5, the web 20 is laterally spaced the same distance along the first and second flanges 30, 40. Alternatively as illustrated in FIG. 6, the web 20 is spaced at laterally different positions along the first and second flanges 30, 40.

Figure 7:
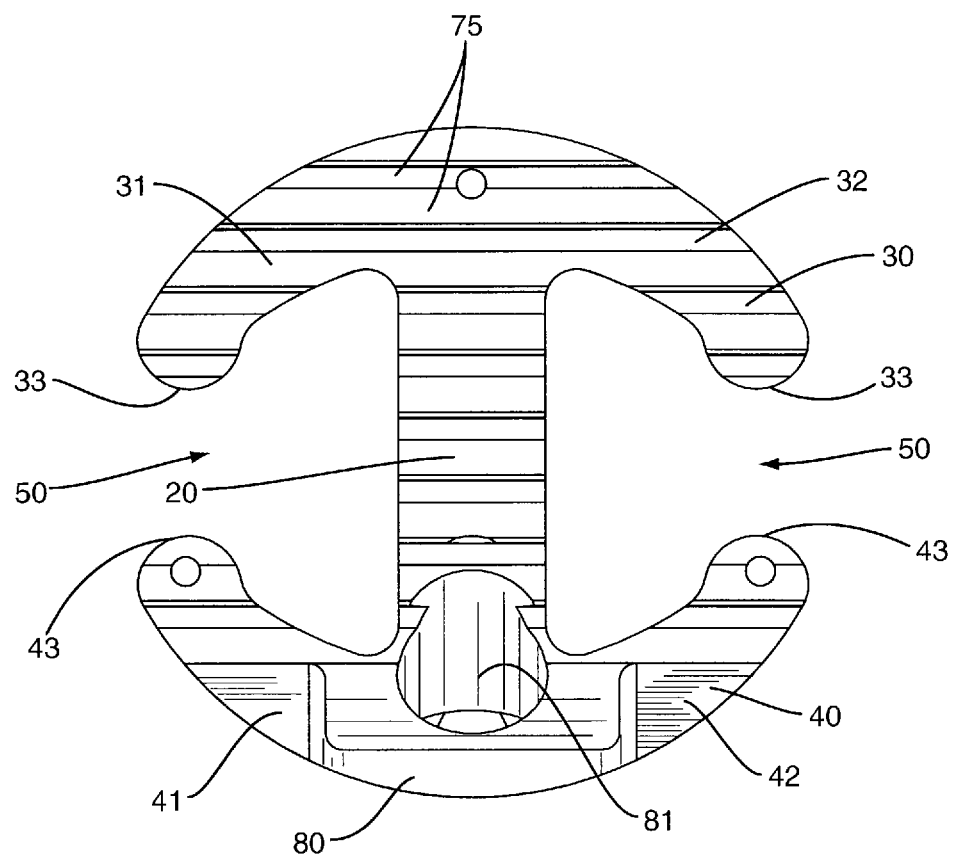
Figure 8:
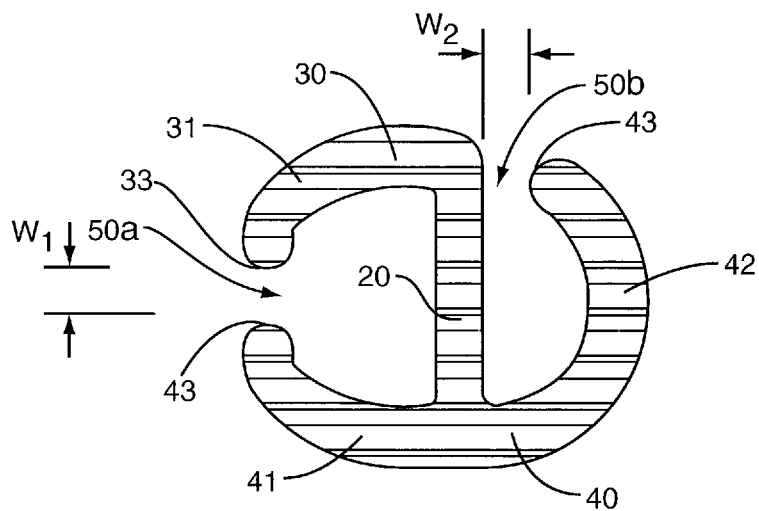

The first and second flanges 30, 40 are space apart along the web 20. The flanges 30, 40 may be the same shape and size, or may include different shapes and sizes. FIG. 7 includes an embodiment with each of the flanges 30, 40 being the same shape and size. FIG. 2 is an embodiment with the first flange 30 including a different shape than the second flange 40. FIG. 8 includes an embodiment with the flanges 30, 40 including different shapes and sizes.

As illustrated in FIG. 2, the first flange 30 may include a first arm 31 that extends outward from a first side of the web 20, and a second arm 32 that extends outward from a second side of the web 20. Each arm 31, 32 includes an end 33 that forms a side of a gap 50. The arms 31, 32 may include the same shape and size as illustrated in FIG. 2, or may include different shapes and/or sizes as illustrated in FIGS. 5 and 6. Likewise, the second flange 40 may include first and second arms 41, 42 as illustrated in FIG. 2. Each arm 41, 42 includes an end 43 that forms a side of a gap 50. Arms 41, 42 may include the same or different shapes and/or sizes.

Figure 9:
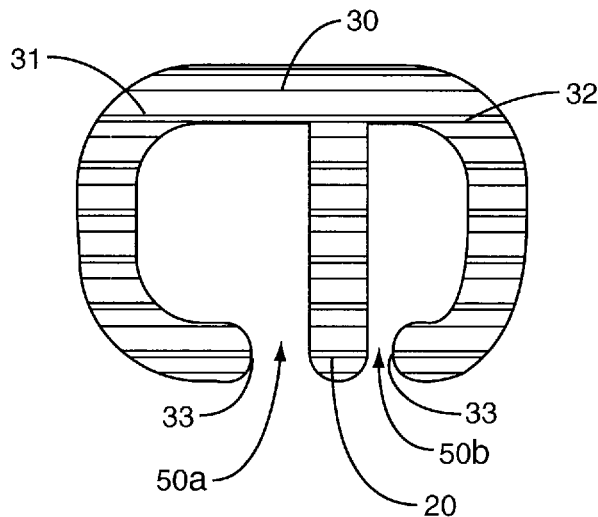

In one embodiment, one of the flanges 30, 40 includes a single arm. FIG. 8 illustrates an embodiment with the first flange 30 including a single arm 31. The first gap 50a is formed between an end 33 of the single arm 31 and end 43 of arm 41. The second gap 50b is formed between the web 20 and the end 43 of arm 42. In one embodiment as illustrated in FIG. 9, the implant 10 includes a single flange 30 (i.e., there is no second flange 40). Each gap 50 is formed between arm ends 33 and the web 20.

Figure 10:
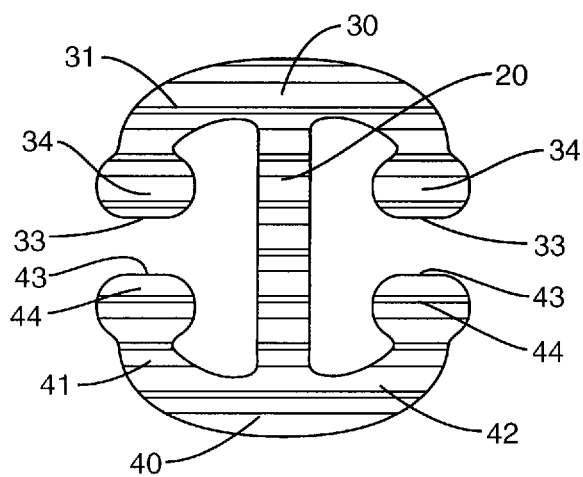

In one embodiment as illustrated in FIG. 10, one or both of the flanges 30, 40 include ends 34, 44 with enlarged widths. The enlarged ends 34, 44 are adjacent to the gaps 50. The enlarged ends 34, 44 include a larger surface area adjacent to the gaps 50 to distribute the forces applied to the implant 10 from the first and second vertebral members and alleviate specific stresses from occurring at the ends 33, 43 of the flanges 30, 40.

Figure 11:
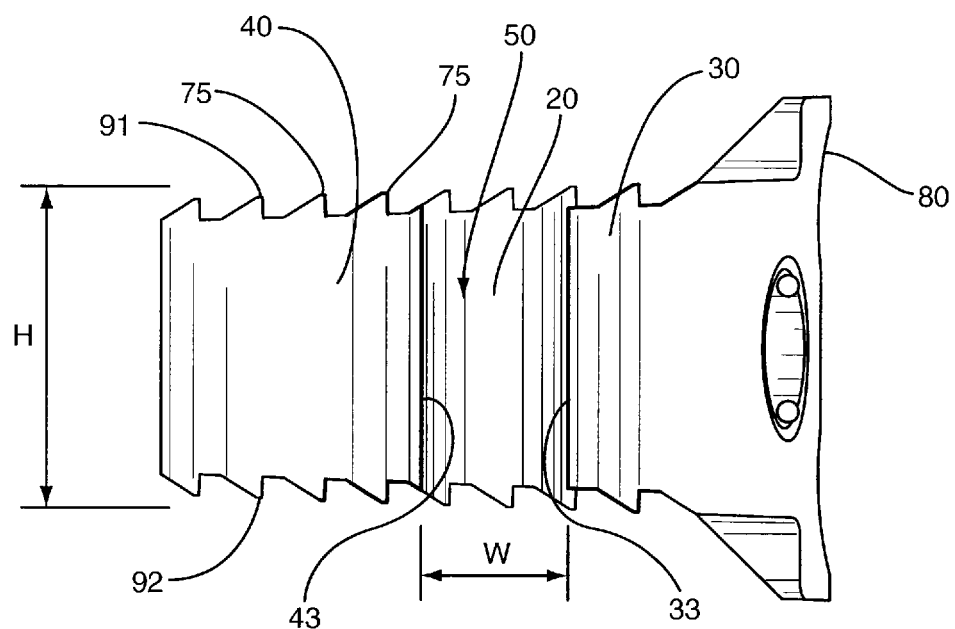
FIG. 11 is a side view of an implant according to one embodiment.
Figure 12:
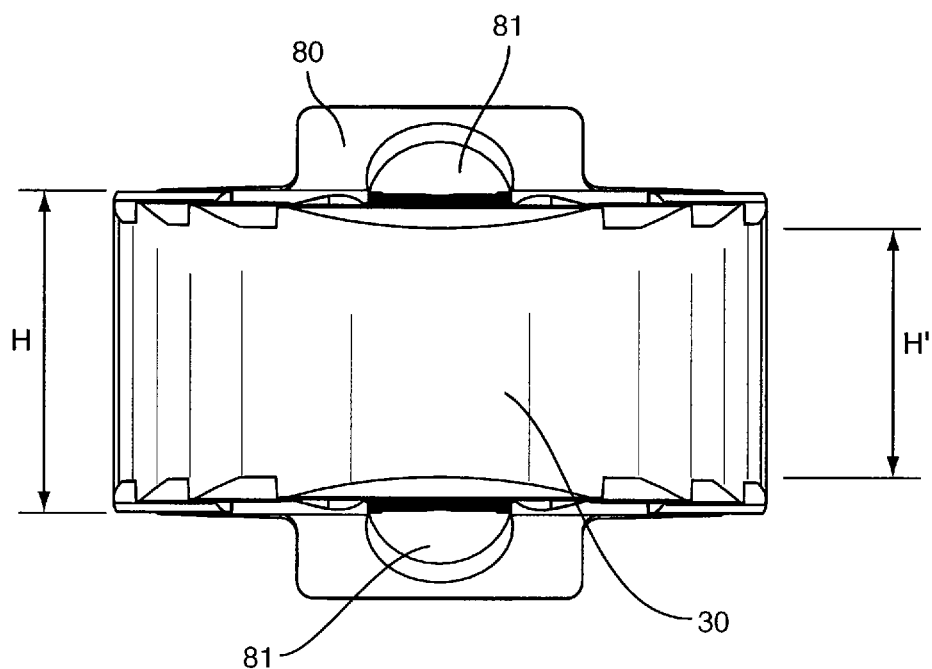
FIG. 12 is a side view of an implant according to one embodiment.

As illustrated in FIG. 11, the implant 10 includes a height H measured between the superior surface 91 and the inferior surface 92. In one embodiment, the height H is substantially the same across the implant 10. In other embodiments, the height H may vary across the implant. FIG. 12 illustrates an embodiment with a portion of the first flange 30 including a smaller height H'. This smaller height facilitates insertion of the implant 10 between the vertebral members with the section with the smaller height H' being initially inserted into the intervertebral space. Various other sections of the implant 10 may include larger or smaller heights depending upon the context of use.

The gaps 50 extend the height H of the implant 10 between the superior and inferior surfaces 91, 92. In one embodiment, the gaps 50 are formed between the arm ends 33, 43 on opposing sides of the web 20. In one embodiment, the gaps 50 are formed between the arm ends 33, 43. In other embodiments, the gaps 50 are formed by an arm end 33 or 43, and the web 20. FIG. 9 includes an embodiment with each of the gaps 50a, 50b formed between ends 33 of the arms 31, 32 and the web 20.

The gaps 50 may include the same or different widths W. FIG. 2 includes each of the gaps 50 with the same width W. FIG. 8 includes a first gap 50a including a width W1 that is larger than the width W2 of the second gap 50b.

Figure 13:
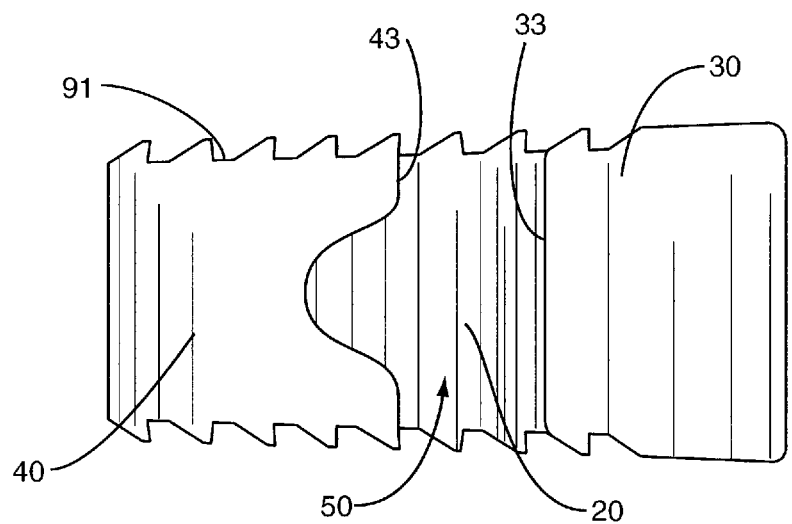
FIG. 13 is a side view of an implant according to one embodiment.
Figure 14:
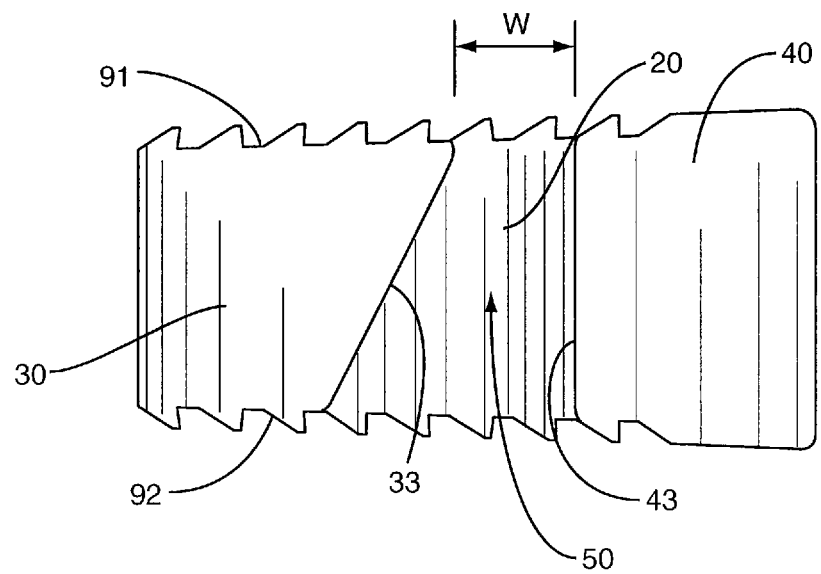
FIG. 14 is a side view of an implant according to one embodiment.

The widths W of the gaps 50 may be constant or may vary along the height. FIG. 11 includes an embodiment with the width W being constant along the height H between the superior and inferior surfaces 91, 92. FIG. 13 includes an embodiment with a variable width with the end 33 of the first flange 30 being straight and the end 43 of the second flange 40 including a curved shape. The ends 33, 43 cause the width W to be larger in the middle of the gap 50 than at the outer ends at the superior and inferior surfaces 91, 92. FIG. 14 includes an embodiment with the gap 50 formed between the first flange 30 and the web 20. The width W is smallest at the superior surface 91 and largest at the inferior surface 92.

Interior spaces 51, 52 are in communication with the gaps 50 and function to contain bone growth material. The spaces are bounded on the lateral sides and are unbounded on the superior and inferior sides. The spaces 51, 52 may include the same or different shapes and sizes. FIG. 2 includes one embodiment with each of the spaces 51, 52 including the same shape and size. Space 51 is positioned inward from the gap 50a and is bounded by the inner edges of arm 31, arm 41, and web 20. Space 52 is positioned inward from gap 50b and is bounded by the inner edges of arm 32, arm 42, and web 20. FIG. 5 includes an embodiment with space 51 being smaller than space 52.

Figure 15:
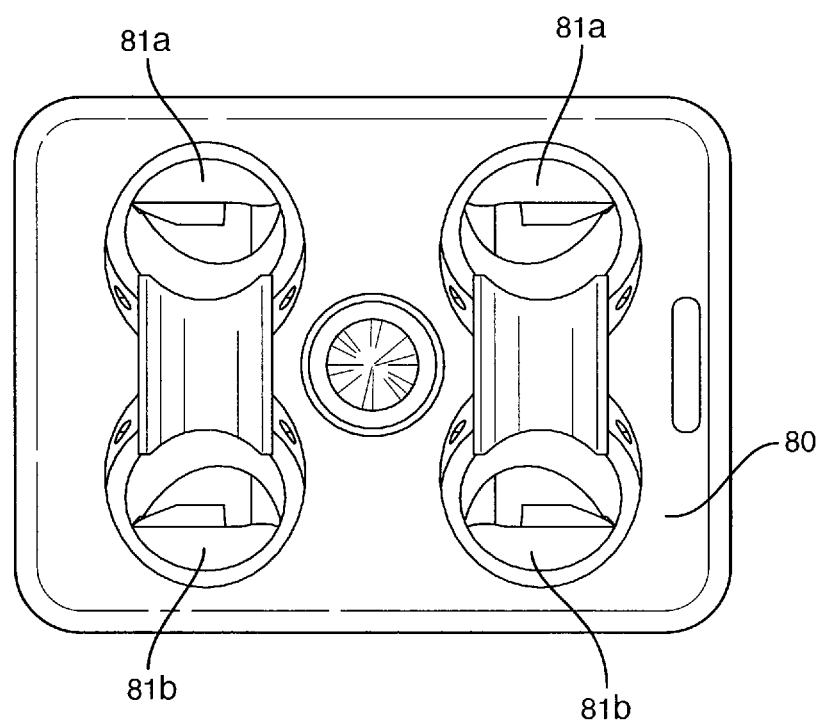
FIG. 15 is a side view of a mount according to one embodiment.

A plate 80 may be formed on a lateral side of the implant 10. The plate 80 may be a separate piece that is attached to the implant, or it may be integrally formed with the body (i.e., the body plate 80 includes a unitary construction). Mount 80 extends above one or both of the superior and inferior surfaces 91, 92 to contact against the lateral sides of the vertebral members to maintain the implant 10 positioned within the intervertebral space. Mount 80 also prevents the implant 10 from being over-inserted into the intervertebral space. One or more apertures 81 may extend through the mount 80. Apertures 81 are sized to receive fasteners (not illustrated) to attach the implant 10 to the vertebral members. In one embodiment as illustrated in FIG. 15, apertures 81a are positioned at a central height of the mount 80 and angle upward towards the superior surface 91 for engaging the fasteners with the first vertebral member. Apertures 81b are angled downward towards the inferior surface 92 to engage the second vertebral member. In one embodiment, as illustrated in FIG. 15, the plate 80 extends across the entire body. In another embodiment as illustrated in FIG. 12, the plate 80 extends across a portion of the body.

The apertures 81 may extend through the plate 80 and into one of the flanges 30, 40 and/or the web 20. FIG. 7 illustrates one embodiment with the aperture 81 extending through the flange 40 and into the web 20. FIG. 2 illustrates an embodiment with the apertures 81 extending through the flange 40 and into the spaces 51, 52 respectively.

Teeth 75 may be positioned on one or both of the superior and inferior surfaces 91, 92. Teeth 75 may include an angled orientation to facilitate insertion of the implant 10 into the intervertebral space, and maintain the proper positioning within the space. Teeth 75 may extend across an entirety or limited sections of the inferior and superior surfaces 91, 92. Embodiments of teeth for an intervertebral implant are disclosed in U.S. patent application Ser. Nos. 11/394,452 and 11/412,330 that are each herein incorporated by reference.

Figure 16:
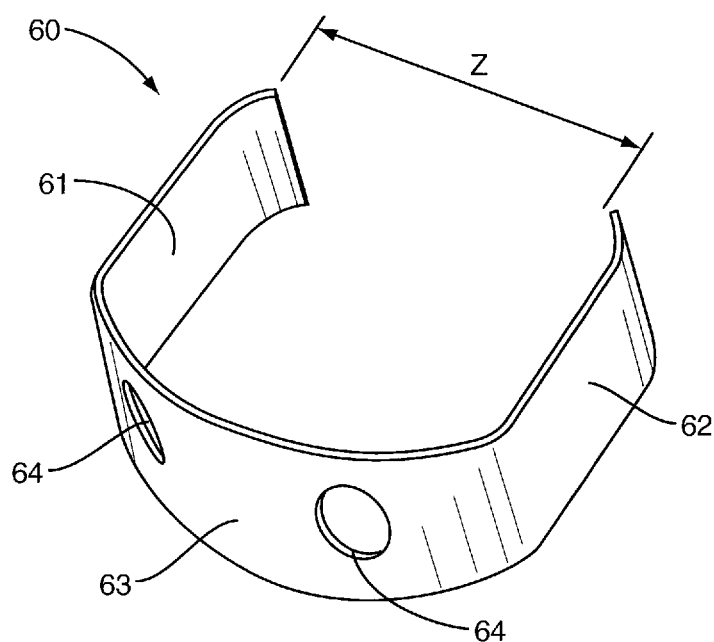
FIG. 16 is a perspective view of a cover according to one embodiment.

A cover 60 may be attached to the implant 10 to extend across one or more of the gaps 50. FIG. 16 illustrates one embodiment of the cover 60 that includes a first section 63 with opposing, spaced-apart arms 61, 62. The cover 60 functions to extend across one or more of the gaps 50 and prevent inadvertent lateral removal of the bone growth material within the spaces 51, 52.

In one embodiment, arms 61, 62 are connected to the first section 63 to be moveable in the directions of arrow Z. This may be caused by the cover 60 being constructed of an elastic material. The cover 60 is sized to deform when inserted onto the spacer 10 with the arms 61, 62 expanding outward. Once attached, the arms 61, 62 apply a compressive force to the exterior lateral sides of the implant 10 to maintain attachment of the cover 60. Apertures 64 may further be spaced about the cover 60 and sized to receive fasteners to further attach the cover 60 to the implant 10.

In another embodiment, arms 61, 62 are movably connected to the first section 63 such as by hinges, pivots, or other like structure. The arms 61, 62 may move apart during attachment of the cover to allow the arms 61, 62 to extend along each side of the implant 10. Once positioned, the arms 61, 62 may move inward to contact against the exterior lateral sides of the implant 10. Apertures 64 may further be positioned around the cover 60 to receive fasteners to attach the cover 60 to the implant 10.

In use, the implant 10 is initially inserted into the intervertebral space. Prior to insertion or after insertion, bone growth material is inserted into the spaces 51, 52. The cover 60 is then attached to the exterior lateral sides of the implant 10. The cover 60 may extend across one or more of the gaps 50 to maintain the bone growth material.

Figure 17:
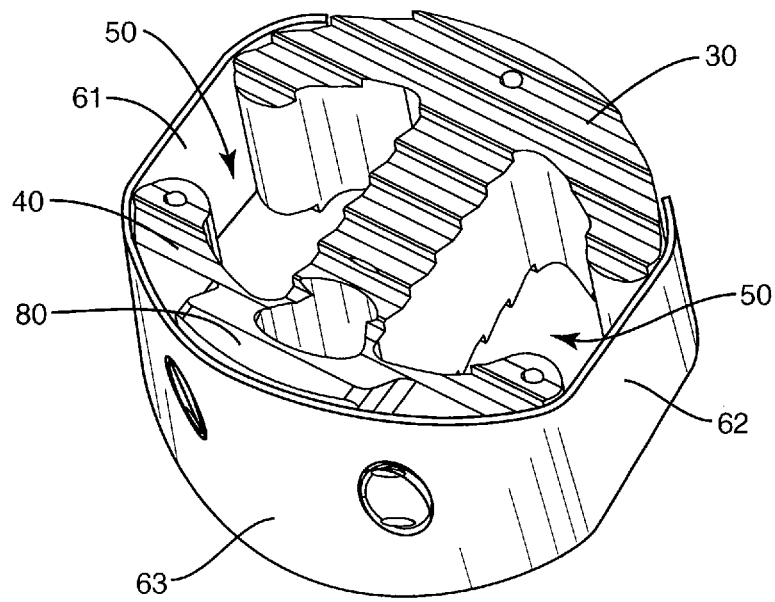
FIG. 17 is a top view of an implant with a cover according to one embodiment.
Figure 18:
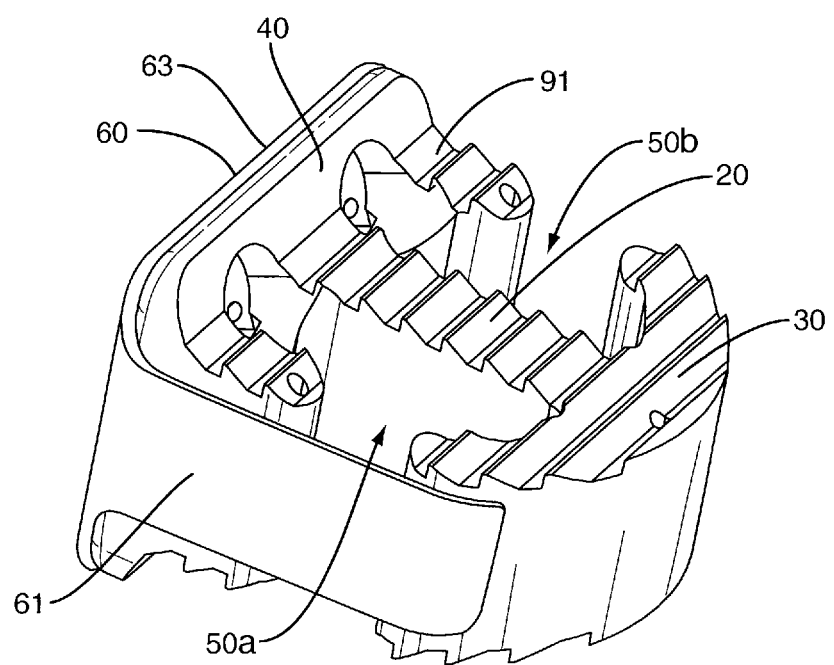
FIG. 18 is a perspective view of an implant with a cover according to one embodiment.

FIG. 17 includes one embodiment with the cover 60 attached to the implant 10. The first section 63 includes a shape to substantially match the second flange 40. Arms 61, 62 substantially match the shape of the second flange 40, and include a length to extend across the gaps 50 and contact against the first flange 30. Cover 60 may also be positioned against the mount 80 and extend over the apertures 81 to prevent back-out of the fasteners. FIG. 18 includes an embodiment with a single arm 61 extending outward from the first section 63. The arm 61 extends across the first gap 50a. In this embodiment, arm 61 includes a smaller height than the gap 50a.

Cover 60 may also be attached to the implant 10 in other manners. In one embodiment, implant 10 includes notches along the exterior lateral side and the cover 60 includes outwardly-extending fingers. During attachment, the fingers slide across the exterior lateral side and mount within one of the notches to maintain the attachment. Other attachments may include snap fits and press fits.

The implant 10 may be inserted into the intervertebral space from a variety of directions. In one embodiment, the implant 10 is inserted in an anterior approach with the mount 80 contacting against the anterior lateral sides of the vertebral members. Other applications contemplate other approaches, including posterior, postero-lateral, antero-lateral and lateral approaches to the spine, and accessing other regions of the spine, including the cervical, thoracic, lumbar and/or sacral portions of the spine.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. An implant to fit within an intervertebral space formed between first and second vertebral members, the implant comprising:
    a body including a web, a first pair of arms extending outward from a first side of the web, and a second pair of arms extending outward from a second side of the web, the body including a height defined by a superior surface configured to contact the first vertebral member and an inferior surface configured to contact the second vertebral member;
    a first gap formed between ends of the first pair of arms and a second gap formed between ends of the second pair of arms, each of the gaps extending the height of the body; and
    a cover that attaches to an exterior lateral side of the body and extends across one of the first and second gaps, the cover including a first section that extends along the body and a first arm that extends along the one of the first and second gaps, the first arm of the cover having a smaller height than the height of the body.

2. The implant of claim 1, further comprising a first space in communication with the first gap and being bounded on lateral sides by the web and the first pair of arms, and a second space in communication with the second gap and being bounded on the lateral sides by the web and the second pair of arms, each of the first and second spaces being unbounded on superior and inferior sides.

3. The implant of claim 2, further comprising an aperture that extends through the height of the web.

4. The implant of claim 1, wherein at least one of the first and second gaps includes a constant width along the height.

5. The implant of claim 1, wherein the body includes a symmetrical shape.

6. An implant to fit within an intervertebral space formed between first and second vertebral members, the implant comprising:
    an elongated web with first and second ends; and
    a first flange positioned at the first end of the web and a second flange positioned at the second end of the web, each of the flanges including a first arm extending outward from a first side of the web and a second arm from a second side of the web;
    each of the flanges including a height defined by a superior surface configured to contact the first vertebral member and an inferior surface configured to contact the second vertebral member;
    the first arms including ends that are spaced apart to form a first gap therebetween on a first side of the web and the second arms including ends that are spaced apart to form a second gap therebetween on a second side of the web, each of the gaps extending the height of the flanges;
    a cover with a first section that extends along one of the first and second flanges and a single extension that extends outward from the first section and across just the first gap and terminates along the other of the first and second flanges away from the first section,
    wherein the extension includes a smaller height than the height of the flanges to be positioned inward from the superior and inferior surfaces when the cover is attached to the flanges.

7. The implant of claim 6, wherein at least one of the gaps includes a constant width.

8. The implant of claim 6, further comprising a first space positioned on the first side of the web and being bounded on lateral sides by the web and the first arms and being unbounded on inferior and superior sides, and a second space positioned on the second side of the web and being bounded on the lateral sides by the web and the second arms and being unbounded on the inferior and superior sides, the first space being in communication with the first gap and the second space being in communication with the second gap.

9. The implant of claim 6, wherein the web is positioned at a middle of the first and second flanges.

10. The implant of claim 6, wherein the web and the first and second flanges form a symmetric body.

11. The implant of claim 6, further comprising a mount positioned on a lateral side of one of the first and second flanges, the mount extending outward beyond the superior and inferior surfaces.

12. The implant of claim 6, wherein the web includes a constant width.

13. The implant of claim 6, wherein each of the first and second flanges includes a curved shape.

14. An implant to fit within an intervertebral space formed between first and second vertebral members, the implant comprising:
- a body including a superior surface to contact the first vertebral member and an inferior surface to contact the second vertebral member, the body including a web and a first pair of arms extending outward from a first side of the web and a second pair of arms extending outward from a second side of the web, each of the arms including an end extending between the inferior and superior surfaces, a height of the web being substantially constant along the length with the superior surface of the web being aligned with the superior surface of the first and second pairs of arms and the inferior surface of the web being aligned with the inferior surface of the first and second pairs of arms;
- a first gap formed between the ends of the first pair of arms and a second gap formed between the ends of the second pair of arms;
- a first space in communication with the first gap and bounded on lateral sides by the web and the first pair of arms, the ends of the first pair of arms being in closer proximity than a remainder of the first pair of arms with a width measured between the first pair of arms being smallest at the first gap and largest within the first space;
- a second space in communication with the second gap and bounded on the lateral sides by the web and the second pair of arms; and
- a cover with a first section that extends along one of the arms of the first pair of arms and a single extension that extends outward from the first section and across just the first gap and terminates along the other arm of the first pair of arms away from the first section, wherein the extension includes a smaller height than a height of the arms such that it is positioned inward from the superior and inferior surfaces when the cover is attached to the arms,
- upon insertion of the implant into the intervertebral space, the gaps and spaces being unbounded on superior and inferior sides.

15. The implant of claim 14, wherein the width of the first gap is equal to a width of the second gap.

16. The implant of claim 14, wherein at least one of the gaps includes a variable width.

17. The implant of claim 14, wherein the cover attaches to an exterior lateral side of the body and extends across at least one of the gaps.

18. An implant to fit within an intervertebral space formed between first and second vertebral members, the implant comprising:
- a body including a central member and first and second flanges extending outward from the central member, the first and second flanges being spaced apart along the central member, the body including an exterior surface formed by one or more of the central member, the first flange, and the second flange, the body further including a height defined by a superior surface configured to contact the first vertebral member and an inferior surface configured to contact the second vertebral member, the height of a first end of the central member being equal to the first flange and the height of a second end of the central member being equal to the second flange such that the central member is sized to contact the first and second vertebral members at multiple locations across the length of the central member between the first and second flanges;
- first and second spaces each formed inward from the exterior surface and extending the height of the body, each of the first and second spaces being partially bounded by the central member;
- a first gap on a first side of the central member, the first gap being in communication with the first space and extending the height of the body; and a second gap on a second side of the central member, the second gap being in communication with the second space and extending the height of the body;
- a first distance between the first and second flanges on the first side of the central member being smallest at the first gap and a second distance between the first and second flanges on the second side of the central member being smallest at the second gap;
- a cover with a first section that extends along one of the first and second flanges and a single extension that extends outward from the first section and across just the first gap and terminates along the other of the first and second flanges away from the first section,
- wherein the extension includes a smaller height than the height of the flanges to be positioned inward from the superior and inferior surfaces when the cover is attached to the flanges.

* * * * *